US00PP22260P2

(12) United States Plant Patent
Kolster et al.

(10) Patent No.: US PP22,260 P2
(45) Date of Patent: Nov. 22, 2011

(54) ***HYDRANGEA* PLANT NAMED 'HOKOMAREVO'**

(50) Latin Name: *Hydrangea macrophylla*
Varietal Denomination: Hokomarevo

(75) Inventors: Peter R. Kolster, Boskoop (NL); Cornelis P. Eveleens, De Kwakel (NL)

(73) Assignee: Kolster Beheer B.V., Boskoop (NL)

( * ) Notice: Subject to any disclaimer, the term of this patent is extended or adjusted under 35 U.S.C. 154(b) by 111 days.

(21) Appl. No.: 12/658,049

(22) Filed: Feb. 1, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner* — Wendy C Haas
(74) *Attorney, Agent, or Firm* — C. A. Whealy

(57) ABSTRACT

A new and distinct cultivar of *Hydrangea* plant named 'Hokomarevo', characterized by its upright plant habit; strong erect stems; relatively small leaves; and mophead-type inflorescences with durable flowers that are initially light red purple in color becoming red purple and light green with development.

4 Drawing Sheets

Botanical designation: *Hydrangea macrophylla.*
Cultivar denomination: 'HOKOMAREVO'.

CROSS-REFERENCED TO RELATED APPLICATIONS

Title: *Hydrangea* Plant Named 'Hokomac' (U.S. Plant patent application Ser. No. 12/658,051).

Title: *Hydrangea* Plant Named 'Hokomathyst' (U.S. Plant patent application Ser. No. 12/658,050).

BACKGROUND OF THE INVENTION

The present invention relates to a new and distinct cultivar of *Hydrangea* plant, botanically known as *Hydrangea macrophylla* and hereinafter referred to by the name 'Hokomarevo'.

The new *Hydrangea* plant is a naturally-occurring whole plant mutation of *Hydrangea macrophylla* 'Xian', not patented. The new *Hydrangea* plant was discovered and selected by the Inventors as a single flowering plant from within a population of plants of 'Man' in a controlled greenhouse environment in Boskoop, The Netherlands in July, 2007.

Asexual reproduction of the new *Hydrangea* plant by vegetative cuttings in a controlled greenhouse environment in Boskoop, The Netherlands since August, 2007, has shown that the unique features of this new *Hydrangea* plant are stable and reproduced true to type in successive generations.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Hokomarevo'. These characteristics in combination distinguish 'Hokomarevo' as a new and distinct cultivar of *Hydrangea* plant:

1. Upright plant habit.
2. Strong erect stems.

3. Relatively small leaves.
4. Mophead-type inflorescences with durable flowers that are initially light red purple in color becoming red purple and light green with development.

Plants of the new *Hydrangea* differ from plants of the parent, 'Xian', in the following characteristics:

1. Plants of the new *Hydrangea* have smaller leaves than plants of 'Xian'.
2. Plants of the new *Hydrangea* are more freely flowering than plants of 'Xian'.
3. Sterile flowers of plants of the new *Hydrangea* have smaller sepals than sterile flowers of plants of 'Xian'.
4. Plants of the new *Hydrangea* and 'Xian' differ in flower color.

Plants of the new *Hydrangea* differ from plants of the *Hydrangeas* 'Hokomac' (U.S. Plant patent application Ser. No. 12/658,015) and 'Hokomathyst' (U.S. Plant patent application Ser. No. 12/658,050) primarily in flower color.

Plants of the new *Hydrangea* can also be compared to plants of *Hydrangea* 'Magical Diamond', not patented. Plants of the new *Hydrangea* differ primarily from plants of 'Magical Diamond' in the following characteristics:

1. Inflorescences of plants of the new *Hydrangea* are flatter than and not as globular as inflorescences of plants of 'Magical Diamond'.
2. Sterile flowers of plants of the new *Hydrangea* have smaller and more durable sepals than sterile flowers of plants of 'Magical Diamond'.

BRIEF DESCRIPTION OF THE PHOTOGRAPHS

The accompanying colored photographs illustrate the unique appearance of the new *Hydrangea* plant, showing the colors as true as it is reasonably possible to obtain in colored reproductions of this type. Colors in the photographs may differ from the color value cited in the detailed botanical description which accurately describe the colors of the new *Hydrangea* plant.

The photograph on the first sheet comprises a side perspective view of a typical plant of 'Hokomarevo' grown in a container.

The photograph on the second sheet is a close-up view of a typical leaf of 'Hokomarevo'.

The photograph on the third sheet is a close-up view of typical developing inflorescences of 'Hokomarevo'.

The photograph on the fourth sheet is a close-up view of a typical fully developed inflorescence of 'Hokomarevo'.

DETAILED BOTANICAL DESCRIPTION

Plants used in the aforementioned photographs and in the following description were grown in two-liter containers during the summer in a shaded glass-covered greenhouse in Boskoop, The Netherlands under conditions which closely approximate commercial production conditions. During the production of the plants, day temperatures ranged from 18° C. to 25° C. and night temperatures ranged from 16° C. to 17° C. Plants of the new *Hydrangea* were six months old when the photographs and description were taken. In the following description, color references are made to The Royal Horticultural Society Colour Chart, 2007 Edition, except where general terms of ordinary dictionary significance are used.

Botanical description: *Hydrangea macrophylla* 'Hokomarevo'.

Parentage: Naturally-occurring whole plant mutation of *Hydrangea macrophylla* 'Xian', not patented.

Propagation:

- *Method.*—By softwood cuttings.
- *Time to initiate roots, summer.*—About three weeks at temperatures of 15° C. to 25° C.
- *Time to initiate roots, winter.*—About five weeks at temperatures of 10° C. to 20° C.
- *Time to produce a rooted young plant, summer.*—About six weeks at temperatures of 15° C. to 25° C.
- *Time to produce a rooted young plant, winter.*—About ten weeks at temperatures of 10° C. to 20° C.
- *Root description.*—Medium in thickness, fibrous; creamy white in color.
- *Rooting habit.*—Moderately branching; medium in density.

Plant description:

- *Form/growth habit.*—Upright plant habit; inverted triangle; strong erect stems; pinching enhances lateral branch development; moderately vigorous growth habit.
- *Plant height.*—About 31.9 cm.
- *Plant diameter or area of spread.*—About 32.3 cm.
- *Lateral branches.*—Length: About 24.2 cm. Diameter: About 7 mm. Internode length: About 3.7 cm. Texture, developing and fully developed: Smooth, glabrous. Angle: Mostly erect to about 10° from vertical. Strength: Strong. Color, developing: Close to 144A to 144B. Color, fully developed: Close to 199B to 199C.

Foliage description:

- *Arrangement.*—Opposite, simple.
- *Length.*—About 13.5 cm.
- *Width.*—About 11.1 cm. Shape: Broadly ovate. Apex: Broadly apiculate.
- *Base.*—Rounded to slightly cordate.
- *Margin.*—Serrate.
- *Texture, upper surface.*—Smooth, glabrous; slightly rugose.
- *Texture, lower surface.*—Smooth, glabrous.
- *Venation pattern.*—Pinnate.
- *Color.*—Developing leaves, upper surface: Close to 141A to 141B. Developing leaves, lower surface: Between 138A and 144A. Fully expanded leaves, upper surface: Slightly darker than between 139A and 147A; venation, close to 144C. Fully expanded leaves, lower surface: Close to 147B; venation, close to 145B.
- *Petiole.*—Length: About 2.9 cm. Diameter: About 4 mm. Texture, upper and lower surfaces: Smooth, glabrous. Color, upper surface: Close to 145A. Color, lower surface: Close to 144B.

Flower description:

- *Flower type and habit.*—Single fertile and sterile flowers arranged on terminal mophead-type panicles; panicles flattened globular; sterile flowers face upright to outwardly and fertile flowers face upright.
- *Fragrance.*—None detected.
- *Natural flowering season.*—Continuous flowering from late spring to late summer in The Netherlands.
- *Flower longevity.*—Sterile flowers last about six weeks on the plant; sterile flowers persistent.
- *Quantity of flowers.*—Freely flowering habit; about 35 fertile flowers and about 400 sterile flowers per panicle.
- *Panicle height.*—About 6.5 cm.
- *Panicle diameter.*—About 11.7 cm.
- *Flower buds, fertile flowers.*—Length: About 3 mm. Diameter: About 2 mm. Shape: Broadly obovate. Color: Close to 186D.
- *Flower buds, sterile flowers.*—Length: About 5 mm. Diameter: About 4 mm. Shape: Obovate. Color: Slightly lighter than 182D tinged with close to 161C to 161D.
- *Fertile flowers.*—Fertile flowers do not open and remain in the bud stage. Shape: Rotate, campanulate. Petals: Quantity: Five. Length: About 2.5 mm. Width: About 1.2 mm. Shape: Ovate. Apex: Acute. Base: Fused. Margin: Entire. Texture, upper and lower surfaces: Smooth, glabrous. Color: When opening, upper and lower surfaces: Close to 195C to 195D. Fully opened, upper and lower surfaces: Close to 195D. Sepals: None observed. Pedicels: Length: About 2 mm. Diameter: About 1 mm. Strength: Moderately strong. Angle: About 10° from vertical. Texture: Smooth, glabrous. Color: Close to 186C to 186D. Reproductive organs: None observed.
- *Sterile flowers.*—Shape: Rotate. Diameter: About 1.8 cm. Depth (height): About 7 mm. Petals: None observed. Sepals: Quantity: Four. Length: About 1 cm. Width: About 1.2 cm. Shape: Broadly deltoid to orbicular. Apex: Rounded. Base: Cuneate. Margin: Entire. Texture, upper and lower surfaces: Smooth, glabrous. Color: When opening, upper surface: Close to 73B. When opening, lower surface: Close to 75B to 75C to close to 186D. Fully opened, upper surface: Close to 67A to 67B, apex close to 146D; with development, close to N155B to N155C to close to 185A to 185B, towards the base, close to 144B to 144C. Fully opened, lower surface: Close to 75B to 75C tinged with close to 145B to 145C; with development, close to N155B to N155C to close to 186B, towards the base, close to 145A to 145B. Pedicels: Length: About 1.4 cm. Diameter: About 1.5 mm. Strength: Strong.

Angle: About 30° from vertical. Texture: Pubescent. Color: Close to 186B to 186C. Reproductive organs: None observed.

*Fruits/seeds.*—Fruit and seed development have not been observed on plants of the new *Hydrangea*.

Disease/pest resistance: Plants of the new *Hydrangea* have not been observed to be resistant to pathogens or pests common to *Hydrangea*.

Temperature tolerance: Plants of the new *Hydrangea* have been shown to be tolerant to temperatures ranging from about −20° C. to about 40° C.

It is claimed:

1. A new and distinct *Hydrangea* plant named 'Hokomarevo' as illustrated and described.

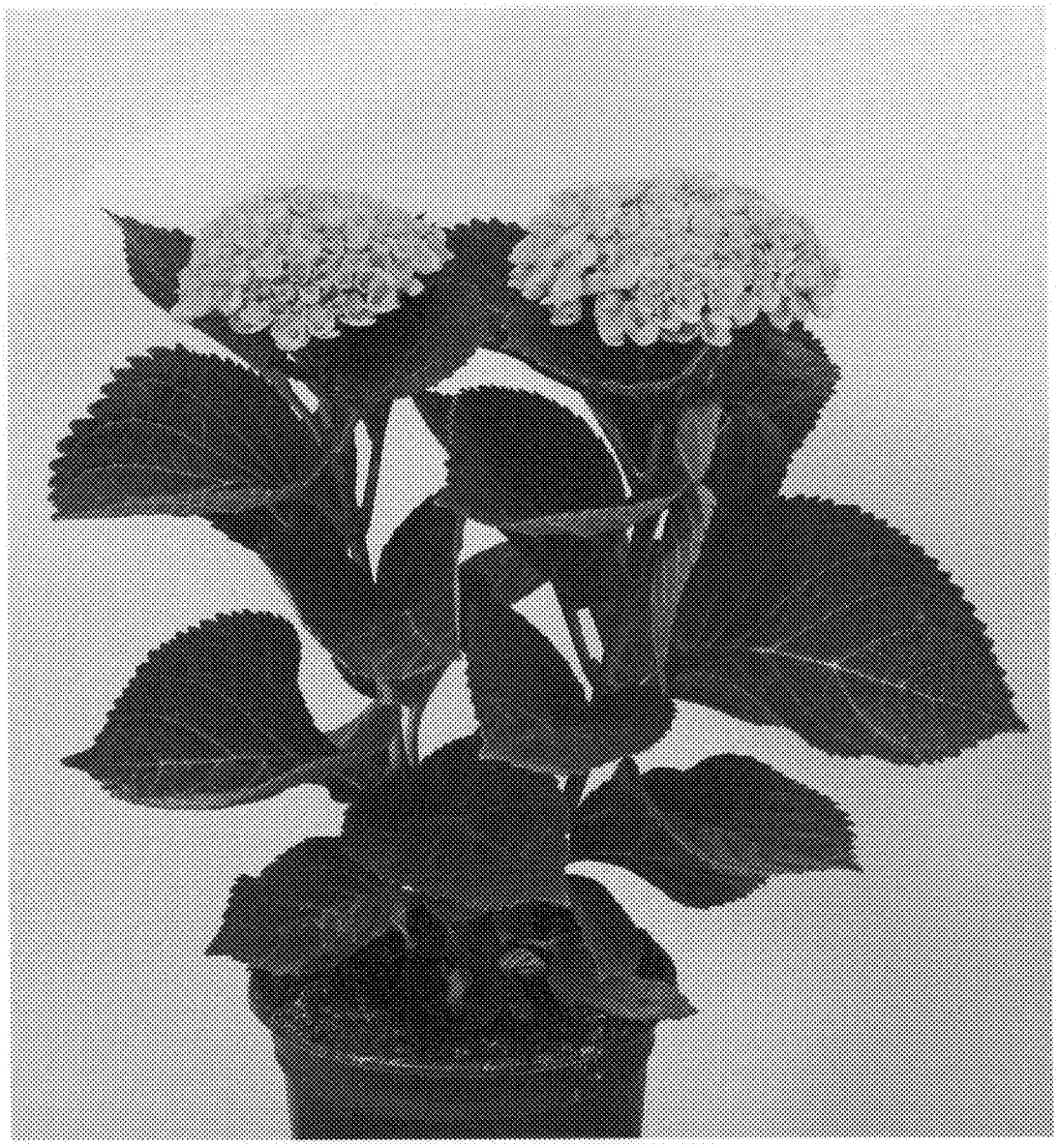

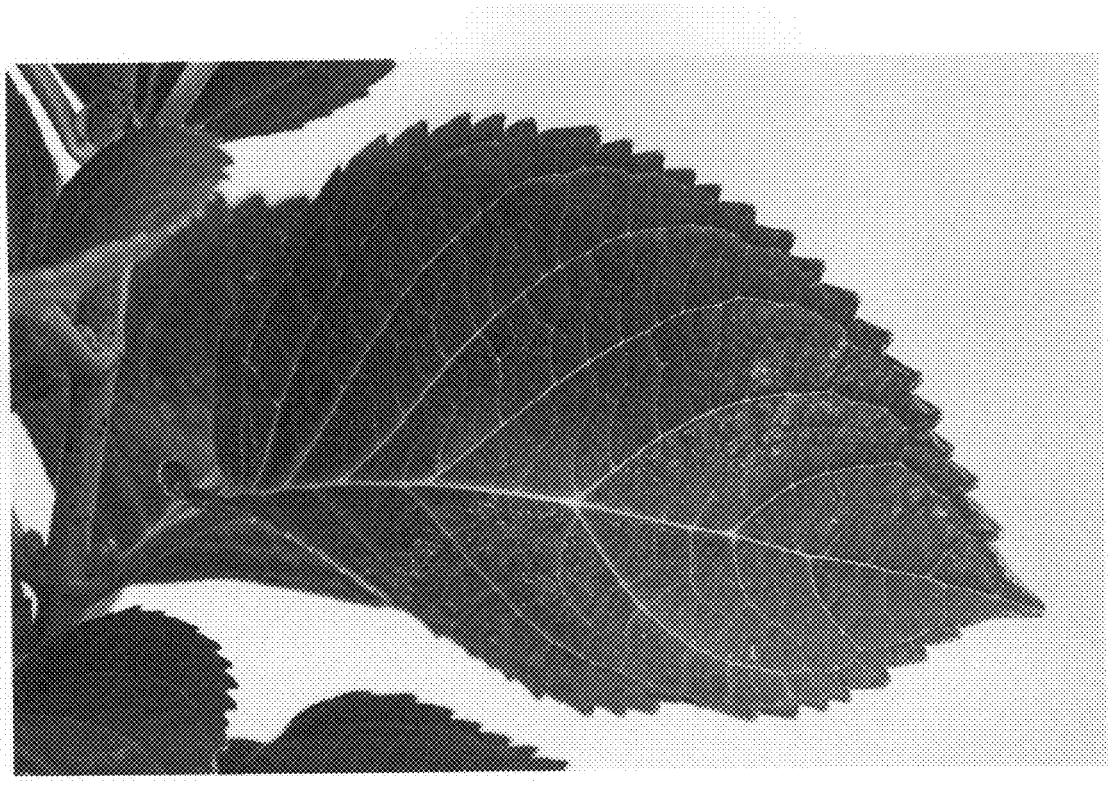

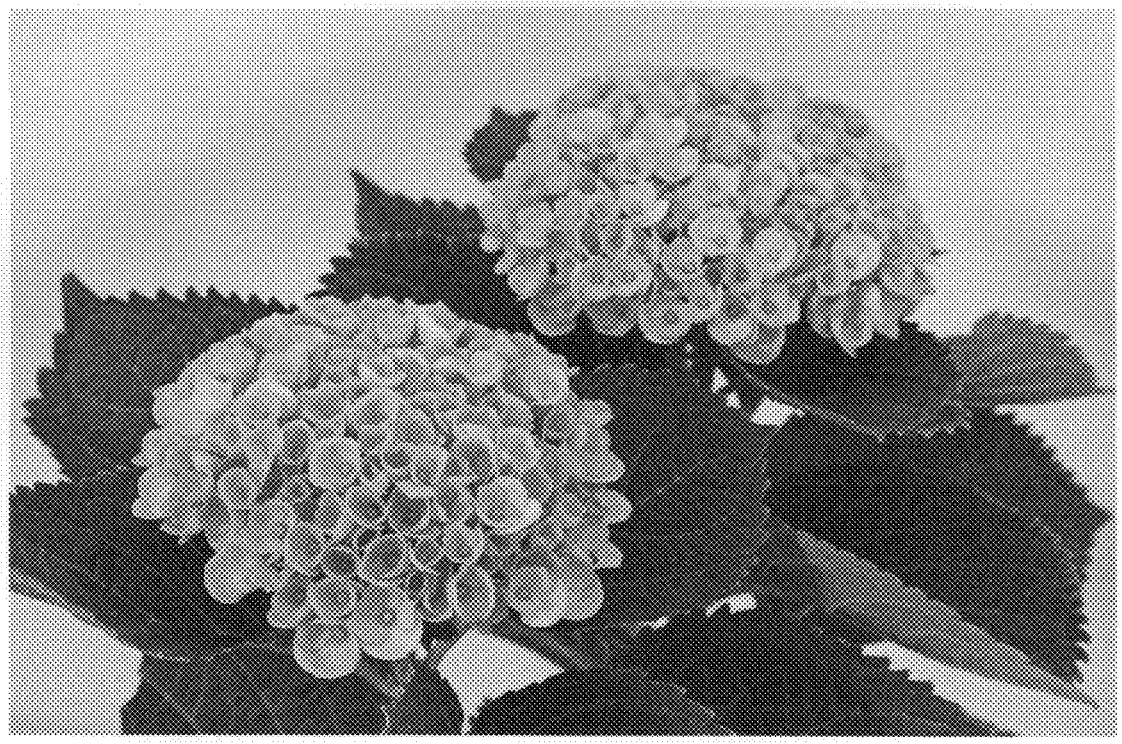

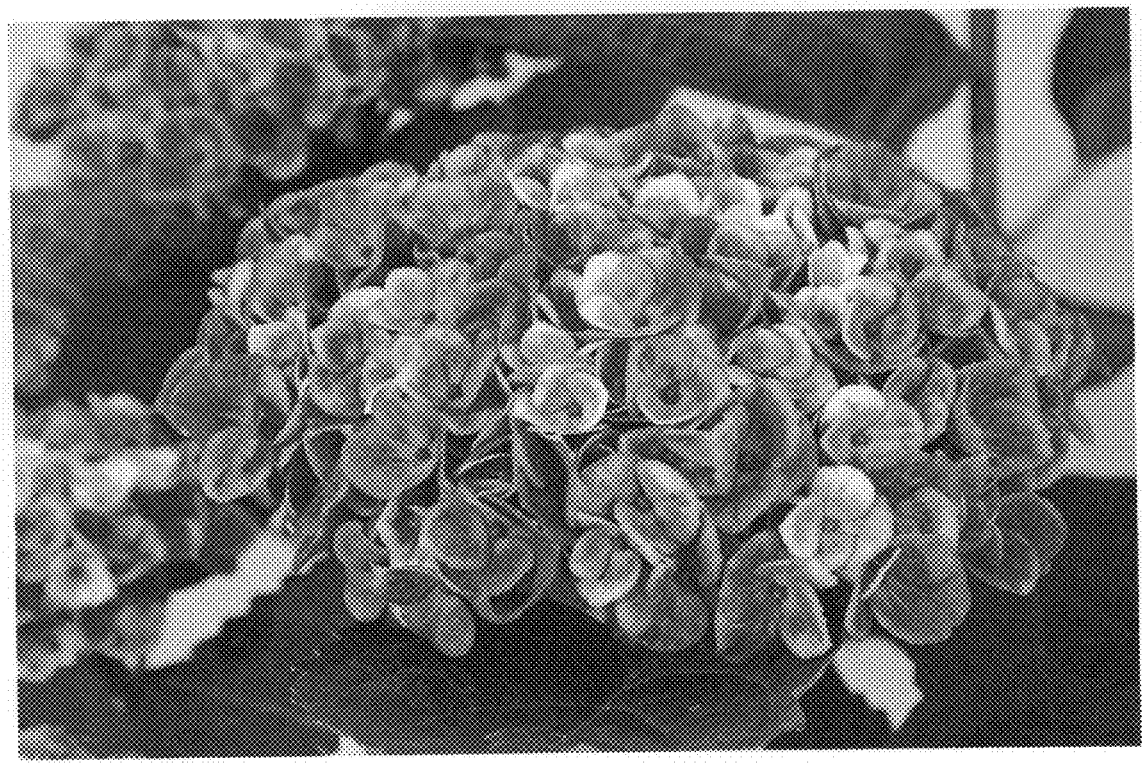

* * * * *